(12) United States Patent
Liu

(10) Patent No.: US 8,846,626 B2
(45) Date of Patent: Sep. 30, 2014

(54) DRUG COMPOSITION FOR TREATING CHRONIC LIVER DISEASE AND ITS APPLICATION

(75) Inventor: Ping Liu, Shanghai (CN)

(73) Assignee: Shuguang Hospital Affiliated with Shanghai University of Traditional Chinese Medicine, Shanghai (CN)

( * ) Notice: Subject to any disclaimer, the term of this patent is extended or adjusted under 35 U.S.C. 154(b) by 5 days.

(21) Appl. No.: 13/219,402

(22) Filed: Aug. 26, 2011

(65) Prior Publication Data

US 2012/0053135 A1 Mar. 1, 2012

(30) Foreign Application Priority Data

Aug. 26, 2010 (CN) .......................... 2010 1 0263205

(51) Int. Cl.
*A61K 36/481* (2006.01)
*A61K 36/484* (2006.01)
*A61K 31/704* (2006.01)

(52) U.S. Cl.
CPC .............. *A61K 36/481* (2013.01); *A61K 31/704* (2013.01); *A61K 36/484* (2013.01); *A61K 2300/00* (2013.01)
USPC .......................................................... 514/26

(58) Field of Classification Search
CPC A61K 36/481; A61K 36/484; A61K 2300/00
USPC .......................................................... 514/26
See application file for complete search history.

(56) References Cited

FOREIGN PATENT DOCUMENTS

CN 101744869 * 6/2010

OTHER PUBLICATIONS

Liu et al. Protective effects of astragaloside IV on porcine-serum-induced hepatic fibrosis in rats and in vitro effects on hepatic stellate cells. J Ethnopharmacol 122:502-508, Feb. 2009.*
Yamamura et al. The pharmacokinetics of glycyrrhizin and its restorative effect on hepatic function in patients with chronic hepatitis and in chronically carbon-tetrachloride-intoxicated rats. Biopharm Drug Dispos 18:717-725, Nov. 1997.*
Derwent 2010-J68679, Jun. 2010, China, Chen et al.*
Glossary of medical education terms, Institute of International Medical Education. http://www.iime.org/glossary.htm Accessed in Mar. 2013.*
Bataller et al. Liver fibrosis. J Clin Invest 115:2009-2018, 2005.*

* cited by examiner

*Primary Examiner* — Brandon Fetterolf
*Assistant Examiner* — Yih-Horng Shiao

(57) ABSTRACT

A drug composition for treating chronic liver diseases, consists of: Astragalus Astragalosides and Glycyrrhiza Acid by weight ratio of 3~6:1. By testing and validating with classic animal model, the results confirmed that the drug composition of the present invention can significantly reduce the collagen content of rat liver, and reduce liver fibrosis and liver injury, wherein the effect is better than the effect of each component alone. The drug composition of the two components or ingredients can improve the anti-hepatic fibrosis, effectively prevent liver fibrosis and promote the development of liver fibrosis reversal, and thus can be used for the treatment and prevention of various chronic hepatitis, liver fibrosis, cirrhosis and other illnesses.

9 Claims, 2 Drawing Sheets

US 8,846,626 B2

DRUG COMPOSITION FOR TREATING CHRONIC LIVER DISEASE AND ITS APPLICATION

BACKGROUND OF THE PRESENT INVENTION

1. Field of Invention

The present invention relates to drug composition for treating chronic liver diseases and its application, and more particularly to drug composition of anti-hepatic fibrosis and liver injury and its application.

2. Description of Related Arts

Liver cirrhosis is the end stage of many chronic liver diseases, and has the morphological character of diffuse liver fibrosis with abnormal node. Liver cirrhosis is a common disease in China, and is also a main disease causing death. China has high incidence of hepatitis B, in which up to 30 millions patients have chronic liver diseases, and 30% of them develop to be liver cirrhosis. There has been definite evidence showing the reversibleness of liver fibrosis or even liver cirrhosis. Interdiction, inhibition or reversal of liver fibrosis is an important objective for treating chronic liver disease. However, there is no chemical or biological agent of anti-hepatic fibrosis in clinical application which is approved by FDA.

The progress in international research is mainly manifested as deep studying on the pathogenesis. An academic authority of liver fibrosis in US, Professor Friedman, has pointed out that continuous specification of the mechanism of liver fibrosis makes effectively treating of anti-hepatic fibrosis possible, but treating of hepatic fibrosis is still a challenging task and there is no effective drug for anti-hepatic fibrosis, so that it requires long-term effort to prepare anti-fibrosis drugs which can be effectively applied to the liver without obvious toxicity.

Chinese patent CN1539483A, published on 2004 Oct. 27, discloses a traditional Chinese medicine for treating chronic liver disease and anti-hepatic fibrosis, belonging to the technical filed of traditional Chinese medicine, which consists of Saffron 3-9 shares, Gecko 3-9 shares, Salvia 4-18 shares, turtle shell 9-24 shares, astragalus 9-30 shares, red ginseng 3-9 shares, Angelica 1-6 shares, Chuanxiong 1-6 shares, Amomum 1-6 shares, bombys batryticatus 1-6 shares, panax notoginseng 3-9 shares, medlar 1-9 shares, radices saussureae 1-6, and is filtered, cleaned, crushed into fine powder, sifted, and equalized. Each 100 grams of powder is mixed with 100 grams of honey per to make pill, and then sterilized with cobalt-60. The invention has been clinically proven to be effective to chronic hepatitis and liver fibrosis, and total efficiency is up to 94%.

Chinese patent CN1985902A, published on 2007 Jun. 27, discloses a traditional Chinese medicine for treating chronic liver disease, prepared according to the principle of "monarch, minister, assistant and guide". The monarch component is raw Atractylodes, and the minister components comprise American ginseng, Polyporus, Poria, and raw Astragalus. The assistant components comprise sarmentosum, snake tongue grass, and capillary artemisia; the guide components comprise Sunburn Gallus gallus domesticus, Salvia, red peony, white peony root. The weight proportion of each component is raw Atractylodes 5% to 18%, American ginseng 1% to 10%, Polyporus 1% to 15%, Poria 0% to 15%, raw Astragalus 5% to 20%, sarmentosum 10% to 50%, snake tongue grass 5% to 30%, capillary artemisia 1% to 15%, Sunburn Gallus gallus 1% to 10%, Salvia 0% to 15%, red peony 1% to 10%, white peony root 1% to 10%, the sum of each component is 100%.

Chinese patent CN101361782A, published on 2009 Feb. 11, discloses a medicine for treating chronic liver disease, adopting the active components or ingredients of the traditional Chinese medicines Cordyceps Polysaccharide, amygdalin, and Gypenosides of a specific ratio to form a drug composition having good efficacy against liver fibrosis and liver damage.

In recent years, the concept of combining disease and syndrome, and syndrome differentially under the guidance of integration concept in traditional Chinese medicine (systems approach), gradually shows clinical features and theoretical advantages to solve this problem, which can not only improve clinical symptoms and liver function, but also significantly improves quality of life of patients, and shows superiority in the inhibition of liver inflammation and fibrosis and promotion of liver fibrosis reversal, etc. In recent decades, the study of liver fibrosis in medicine has made remarkable progress in China. Since 2000, there have been Fufang-biejia-rangan film, Fuzhenghuayu capsules (tablets) and other national anti-fibrosis drugs used in clinical medicine, wherein Fuzhenghuayu film has been approved by the FDA in the United States to carry out phase II clinical trial of anti-hepatic fibrosis of hepatitis C. The effect of traditional Chinese medicine against liver fibrosis is achieved through multi-channel, multi-level effect, and thus showing a combined effect, adapted to the development of liver fibrosis in the complex pathological mechanisms, which is the advantage of integration concept in traditional Chinese medicine.

In past two decades, a number of domestic and international researches have been carried out for active components or ingredients in traditional Chinese medicine of anti-hepatic fibrosis, and some active components or ingredients of traditional Chinese medicine having effects of anti-hepatic fibrosis are found. However, both traditional Chinese herbal compound, and a single active ingredient, has their shortcomings. Due to the complex composition of traditional Chinese herbal compound, quality control difficulties, poor stability, it is one of the problems for internationalization of the traditional Chinese medicine. Single component or ingredient is often difficult to obtain a good effect, but effective dose may bring obvious side effects. Therefore, eliminating side effect but maintaining the advantage of treating complex diseases of the traditional Chinese medicine compound, is a major problem, as well as one important direction of developing traditional Chinese medicine for anti-hepatic fibrosis.

SUMMARY OF THE PRESENT INVENTION

A technical problem to be solved by the present invention is to provide a drug composition of improving liver fibrosis and liver injury and effectively treating chronic liver diseases, and provide the use of the drug composition.

In order to solve the technical problem, the present invention uses the mathematical model "uniform design" and analysis techniques of the orthogonal design, based on the prior art, carries out research of effective components/ingredients compatibility of anti-hepatic fibrosis, and uses active components or ingredients of traditional Chinese medicine, Astragalus Astragalosides and Glycyrrhiza Acid, to filter out the drug composition of anti-hepatic fibrosis and liver damage.

The drug composition is composed of two components or ingredients of Astragalus Astragalosides and Glycyrrhiza Acid. The weight ratio of Astragalus Astragalosides and Glycyrrhiza Acid is 3~6:1, wherein Astragalus Astragalosides comes from astragalus, and Glycyrrhiza Acid comes from traditional Chinese medicine, liquorice.

The method of extracting Astragalus Astragalus from astragalus and Glycyrrhiza Acid from licorice is the same as conventional methods in the prior art. The drug composition of the present invention has no special preparation methods. Astragalus Astragalosides and Glycyrrhiza Acid is weighed by ration, and prepared into clinical preparation including tablets, granules, capsules and other oral solid preparation forms.

The drug composition of the present invention is experimented by the classic animal models of liver injury and liver fibrosis induced by Dimethylnitrosamine (DMN), and bile duct ligation (BDL), wherein intervention is involved in the model development process, and the drug composition is filtered out and repeatedly tested by use of "uniform design" and "orthogonal design". The results confirmed that the drug composition of the present invention can significantly reduce the collagen content of rat liver, and reduce liver fibrosis and liver injury, wherein the effect is better than the effect of each component alone. The drug composition of the two components or ingredients can improve the anti-hepatic fibrosis, effectively prevent liver fibrosis and promote the development of liver fibrosis reversal, and thus can be used for the treatment and prevention of various chronic hepatitis, liver fibrosis, cirrhosis and other illnesses.

These and other objectives, features, and advantages of the present invention will become apparent from the following detailed description, the accompanying drawings, and the appended claims.

DETAILED DESCRIPTION OF THE PREFERRED EMBODIMENT

Figure 1:
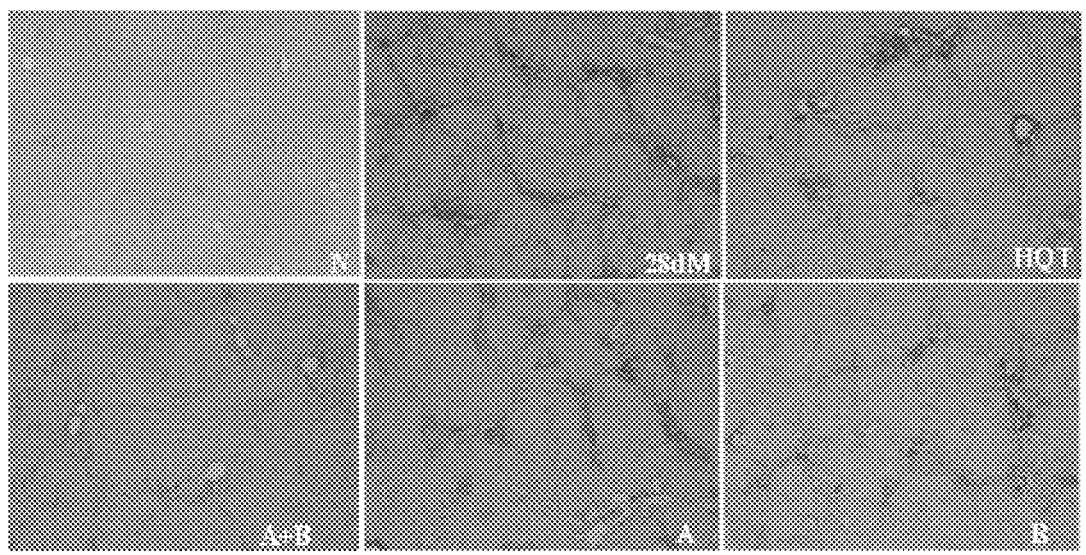
FIG. 1 is staining photographs (×100) of liver tissues of rats in each group by Sirius red collagen according to embodiment 1 of the present invention.

The beneficial effect of a drug composition of the present invention is confirmed by the following embodiments:

Embodiment 1

The DMN-induced rat liver fibrosis model and analysis of orthogonal design is used to obtain the optimal ratio of the composition to lower collagen content in the liver.

1. Materials and Method:
1.1 Experimental Animals

160 Wistar male rats, (40 in normal group, 120 in in the model group), clean level, body weight (150±10) g, provided by the Shanghai Experimental Animal Center of Chinese Academy of Sciences, and is fed, modeled, and observed in Clean Animal room of Shanghai Medical University Experimental Animal Center, free access to water.

1.2 Preparation and Equipments

Dimethylnitrosamine, DMN, and hydroxyproline, Hyp, standard products, Tokyo Kasei Kogyo Co., Ltd.; liver function kit, purchased from Nanjing Jiancheng Bio-Products Corporation; DAB Kit, Beijing Zhongshan Golden Bridge Biotechnology, batch number: 50681680; paraformaldehyde, China Medicine Group Shanghai Chemical reagent, chemical pure, batch number: F20030117, fetal calf serum and SABC kit, purchased from Wuhan Boster Company; α-SMA, purchased from SIGMA Corporation; TGF-β1, Mouse Monoclonal IgG, purchased from Abcam company (ab27969), 1:2000 dilution; Smad5, Rabbit Monoclonal IgG, purchased from Epitomics, Inc. (1682-1), 1:1000 dilution; P-Smad1/5/8, Rabbit Monoclonal IgG, purchased from Epitomics (2737-1), 1:500 dilution; Smad7, Rabbit Polyclonal IgG, purchased from BioVision (3670-100), 1:100 dilution; BMP7, Rabbit Monoclonal IgG, purchased from Abcam (ab56023), 1:2000 dilution; STAT1, Mouse Monoclonal IgG, purchased from Abcam (ab78112), 1:200 dilution; P-STAT1, Mouse Monoclonal IgG, MILLIPORE (05-1064), 1:500 dilution; Arkadia, Mouse polyclonal IgG, purchased from Abcam (ab885351), 1:1000 dilution; GAPDH, Mouse Monoclonal IgG, purchased from Kangchen company (KC-5G4), 1:5000 dilution; near-infrared dye (Alexa680) labeled goat anti-rabbit IgG polyclonal dual antibody and near-infrared dye (IRD800) labeled donkey anti-mouse IgG polyclonal secondary antibody, both Li-COR products. Revert Aid™ First Strand cDNA Synthesis Kit, # K1622, Ferments Life Sciences, purchased from Haimaiyueer Biotechnology Co., Ltd.; quantitative PCR kit, SYBR Green Ex Taq™ (perfect Real Time), Lot: DRR041A, Takara Biotechnology (Dalian) Co. Ltd. Professional Image-Pro Plus 6.1 image analysis software purchased from Media Cybernetics Corporation; Olympus IX70 microscope, purchased from Olympus Optical Company; Odyssey scanner and Odyssey two-color infrared laser imaging system, both Li-COR products; PCR cycler Rotor-Gene RG-3000, Gene Company Ltd. products; Cycler PCR instrument, BIO-RAD products.

1.3 Medicines

Astragalus Astragalosides, A: derived from Astragalus, Xi'an Hongsheng Biotechnology Co., Ltd. products, specifications 90%; Glycyrrhiza Acid, B: derived from licorice, Nanjing Zelang Medical Technology Co., Ltd. products, specifications 98%.

Astragalus Astragalosides and Glycyrrhiza Acid are mixed by weight ratio 3:1, 4:1, 5:1 and 6:1, drug composition A+B in different proportions are randomly selected for subsequent experiments.

1.4 Modeling

Referring to Ala-Kokko method of modeling (Ala-Kokko L, Pihlajaniemi T, Myers J C et al. Gene expression of type I, III and IV collagens in liver fibrosis induced by dimethylnitrosamine in the rat. *Biochem J* 1987; 244: 75-9.) DMN is diluted with saline into 0.5% solution, in the model group, 120 rats are intraperitoneally injected by 2 ml/g body weight dose, once per day, on the beginning 3 days of a week, for 4 weeks. In normal control group, 40 rats are intraperitoneally injected with normal saline of same dose.

1.5 Grouping and Administrating

Respectively at the end of three days of modeling, the end of two weeks of modeling, the end of three weeks of modeling, and the end of four weeks of modeling, 10 normal rats, 10 model rats are observed as a model of dynamic observation. Starting from the end of 2 weeks of modeling, the model rats were randomly divided into 1-6 groups of orthogonal design and model group, each having 10 rats. While continuing modeling, the groups of orthogonal design are intervened by eight times of clinical dose amount of a 65 kg adult body weight, administrated respectively in accordance with design amount. Before using, the drug composition is diluted with 10 ml of distilled water, and is processed with intragastric administration according to 10 ml/kg rat body weight dose, once daily for 2 weeks. And normal control rats (10) and model control group (10) are set; rats in the normal group and the model control groups are processed with intragastric administration by the same volume of distilled water.

1.6 Experimental Projects

Astragalus glycosides A, Glycyrrhiza Acid, B, and drug-composition A+B are factors for evaluation, each factor were set from two levels (level 1=administration, level 2=no), to obtain the orthogonal design. Model groups and normal groups are set.

1.7 Statistical Methods

Measurement data is expressed as x̄±s, the SAS 9.1.2, DAS 2.1.1 and SPSS16.0 statistical software are used to process data, and single-factor analysis of variance is used for comparisons between multiple groups.

2. Result

A small amount of collagen fibers is only seen in the portal area and central vein wall of normal liver tissues. After modeling 4 weeks with DMN, hyperplasia of collagen fibers separates the lobular hepatis to form a coarse, dense full interval, the normal lobular structure disappears, some forms incomplete false lobules, 89% of the model rats has formed liver fibrosis of stage III. Hyperplasia of collagen fibers in the rats in groups of administration is improved in various degrees; the fiber spacing is narrow, loose and incontinuous, see FIG. 1.

Hydroxyproline content analysis shows that, as compared with model group, hydroxyproline content in liver tissue of rats in the A+B group is significantly lower ($P<0.01$) than the model control group of four weeks, see Table 1.

TABLE 1 hyperplasia stages of rat liver collagen in each group

| group | n | Hyp(μg/g) | hyperplasia stages of rat liver collagen | | | |
|---|---|---|---|---|---|---|
| | | | 0 | I | II | III |
| N | 10 | 237.82 ± 24.92 | 10 | 0 | 0 | 0 |
| 28dM | 9 | 650.44 ± 117.08** | 0 | 0 | 1 | 8 |
| A + B | 9 | 481.92 ± 94.12## | 0 | 1 | 7 | 1 |
| A | 9 | 583.98 ± 118.00 | 0 | 0 | 6 | 3 |
| B | 9 | 595.74 ± 109.74 | 0 | 0 | 5 | 4 |

Note:
compared with the normal control group of the same period,
**$P<0.01$;
compared with the model group of the same period,
$P<0.01$.

Compared with normal group, after modeling for 4 weeks, the serum ALT, AST, ALP activity and TBil content is significantly increased ($P<0.01$) in model rats. And as compared to 4-weeks model group, serum ALT activity in the A+B group is significantly decreased ($P<0.01$); serum AST activity in the A+B and A group is significantly decreased ($P<0.05$); serum ALP activity in the A+B and B group is significantly lower than the 4-weeks model control group ($P<0.01$); serum TBil activity in B group is also significantly lower than the 4-weeks control group ($P<0.05$). The result is shown in Table 2.

The combination of A+B reduces liver Hyp content and serum ALT activity most significantly; the combinations of A, and A+B reduce the AST most significantly; the combinations of A, and A+B improve the content of Alb most significantly; the combinations of B, and A+B reduce the ALP most significantly. In summary, A and B have synergistic reduction of serum ALT activity and liver hydroxyproline content and significant improvement the stages of liver fibrosis; B is the main component to reduce the content of TBil, A has a significant reduction effect to AST.

Astragalus glycosides and Glycyrrhiza Acid alone or combined both reduces generating of TGF-β1 significantly better than the original astragalus soup, wherein Astragalus glycosides alone has best effect.

Increasing negative regulation of signal transduction of Smad7 protein to TGFβ1 is the primary mechanism of synergistic effect to liver fibrosis by the compatibility of Astragalus glycosides and Glycyrrhiza Acid. And synergistic promotion of Smad7 and inhibition expression of TGFβ1 signal transduction may be possibly through IFN-γ/JAK/STAT1, ubiquitin-proteolytic enzyme composition body pathway, and other signaling pathways.

Astragalus glycosides and Glycyrrhiza Acid, alone or in combination group can significantly increase BMP-7mRNA, protein and protein expression of P-Smad1/5/8 of liver fibrosis in rat liver tissues by DMN. This application pathway will not only promote the expression of Smad7 but also inhibit signal transduction of TGFβ1, and increased expression of BMP7 protein have the combined effect of protecting liver cells and promoting regeneration of liver cells on liver fibrosis.

Embodiment 2

Effect of active component compatibility of Astragalus soup of anti-hepatic fibrosis for rats of bile duct ligation 1. Materials and Method:
   1.1 Experimental Animals
   83 SD male rats, SPF grade, weighing 200~220 g, by the Shanghai Experimental Animal Center of Chinese Academy of Sciences, Certificate of Conformity: SCXK (Shanghai) 2010-0005, fed on the Shanghai Medical University Experimental Animal Center, free access to water.
   1.2 Medicines
   Astragalus Astragalosides, AS: same with experiment 1.
   Glycyrrhiza Acid, GA: same with experiment 1.
   Astragalus soup: same with experiment 1.
   Ursodeoxycholic acid, UDCA: purchased from Dr. Falk Pharma GmbH.

TABLE 2

| | | Serum liver function (x̄ ± SD) | | | | |
|---|---|---|---|---|---|---|
| group | n | ALT(U/L) | AST(U/L) | Alb(g/L) | ALP(K/100 ml) | TBil (μmol/L) |
| N | 10 | 16.49 ± 6.95 | 27.74 ± 12.88 | 34.30 ± 2.46 | 28.47 ± 4.15 | 7.30 ± 2.24 |
| 28dM | 9 | 63.71 ± 16.45** | 83.10 ± 21.38** | 23.53 ± 3.26** | 68.20 ± 10.81** | 16.82 ± 6.89** |
| A + B | 9 | 32.22 ± 14.68## | 63.69 ± 14.12# | 25.56 ± 3.67 | 46.17 ± 8.69## | 12.67 ± 10.68 |
| A | 9 | 59.12 ± 16.25 | 66.02 ± 10.93# | 25.44 ± 2.15 | 57.56 ± 13.67 | 14.19 ± 5.33 |
| B | 9 | 55.18 ± 17.12 | 76.61 ± 14.09 | 23.11 ± 5.52 | 38.77 ± 17.84## | 10.23 ± 5.42# |

Note:
compared with the normal control group of the same period,
*$P<0.05$,
**$P<0.01$;
compared with the model group of the same period,
$P<0.05$,
$P<0.01$.

1.3 Preparation and Equipments

The same with experiment 1.

2. Methods 2.1 Modeling Preparation

Model rats (75 rats) are cut along the ventral midline, exposing the common bile duct, conversely injected hardener into hilus hepatis, ligating proximal and distal ends of the common bile duct, cutting the middle, closing the abdomen for 4 weeks. Sham-operated rats (8 rats) only have abdomen cut, and closed after freeing the common bile duct.

2.2 Grouping and Administrating

Starting from the first day of $2^{nd}$ week of modeling, the model rats were randomly divided into 5 groups of astragalus soup, A/B combination, A alone, B alone, and UDCA, each group has 12 rats. While continuing modeling, the groups of administration are intervened by eight times of clinical dose amount of a 65 kg adult body weight. Before using, the drug compositions of astragalus soup, A/B combination, A alone, B alone, and UDCA (UDCA: 80 mg·kg$^{-1}$·d$^{-1}$, ig) are respectively diluted with 10 ml of distilled water, and is processed with intragastric administration according to 10 ml/kg rat body weight dose, once daily for 3 weeks. And sham-operation control rats (8) and model control group (15) are set; rats in the normal group and the model control group are processed with intragastric administration by the same volume of distilled water.

2.3 Collecting and Processing of Samples

At the end of $4^{th}$ week, rats are executed to obtain test samples. HE staining and collagen staining of liver tissue, liver tissue Hyp content, serum liver function: ALT, aspartate aminotransferase, AST, and activity of alkaline phosphatase, ALP, albumin, Alb, and total bilirubin, TBil content.

2.4 Statistical Methods

The same with experiment 1.

3. Result

Figure 2:
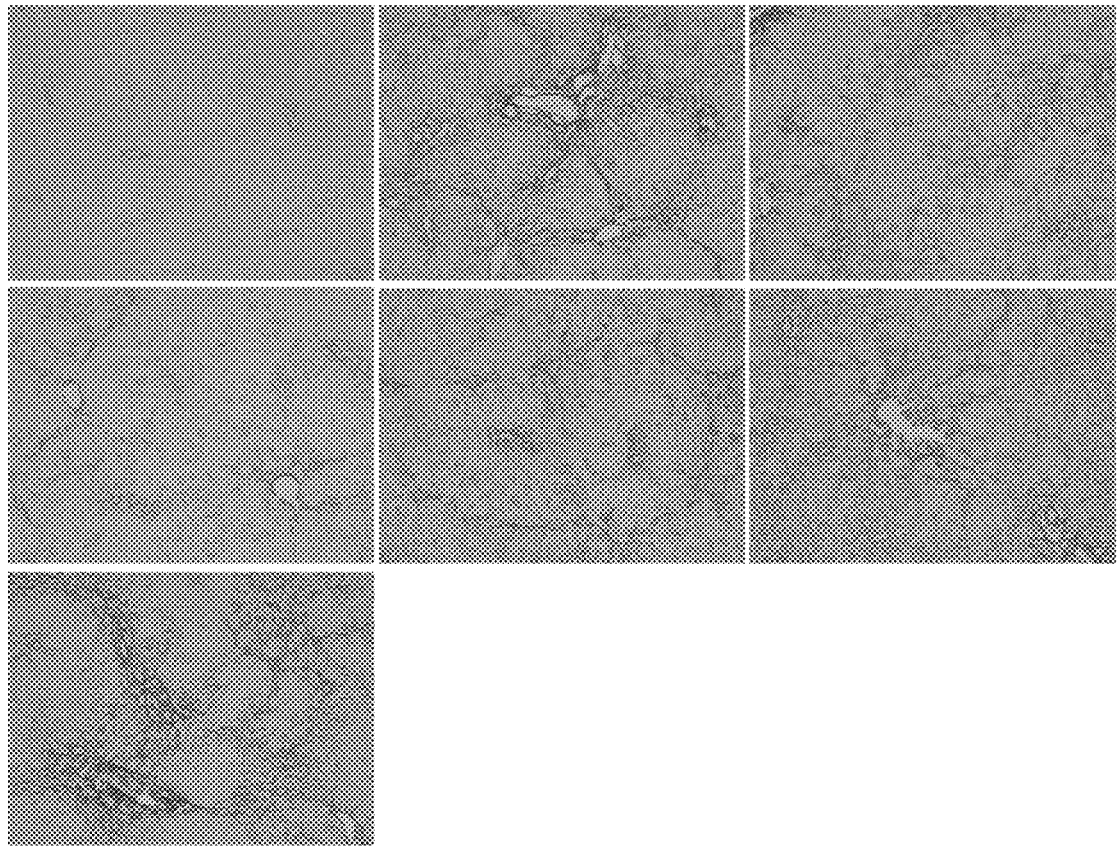
FIG. 2 is staining photographs (×100) of liver tissues of rats in each group by Sirius red collagen according to embodiment 2 of the present invention.

Among the BDL model rats, there are 31 deaths in modeling of 4 weeks, mortality rate is 37%. Serum liver function is significantly abnormal, liver Hyp content is significantly increased, HE staining of liver tissue shows bile duct epithelial cells gradually increase, large amount of collagen deposition is observed around the proliferation of biliary epithelial cells, normal liver cells gradually decrease, inflammation and necrosis is slight, forming a typical cholestatic liver fibrosis. Although UDCA can significantly reduce serum transaminase activity ($P<0.05$) as compared with the model group, no significant histological improvement is observed, so the drug can not prevent liver fibrosis process induced by cholestasis. A/B combination can significantly improve pathological changes of liver fibrosis in BDL rats, which is similar to effect of Astragalus soup, wherein liver Hyp content (decreased 27.3% as compared with the model group of the same period) is lower than the astragalus soup group (decreased 18.4% as compared with the model group of the same period), but no significant difference is observed; and serum ALT activity is significantly lower than Astragalus soup group ($P<0.05$); the effect that A and B combination group decreases liver Hyp content and serum ALT is significantly better than B alone group and the UDCA group ($P<0.05$); the effect that A and B combination group decreases serum ALT is significantly better than A alone group ($P<0.05$), and A and B combination group can significantly lower serum AST, ALP activity and TBil content, increase serum Alb content ($P<0.05$); in addition, A along group has significant effect ($P<0.05$) in reducing the Hyp content in liver tissue, serum AST, ALP activity and TBil content, B alone group has significant effect ($P<0.05$) in reducing ALP activity and TBil content, see FIG. 2, Tables 3 and 4.

TABLE 3 rats in each group biliary liver fibrosis scores and liver tissue Hyp content changes ($\bar{x} \pm s$)

| group | n | Hyp(μg/g, wet liver weight) | integral |
|---|---|---|---|
| N | 8 | 199.37 ± 35.26 | 0 |
| 28 dM | 7 | 801.28 ± 65.90** | 7.29 ± 0.76** |
| HQT | 8 | 676.91 ± 65.48## | 5.13 ± 0.99## |
| A + B | 9 | 629.30 ± 95.01## | 4.44 ± 0.73## |
| A | 8 | 705.71 ± 46.52# | 6.38 ± 0.92# |
| B | 6 | 772.00 ± 86.81$ | 6.50 ± 0.84$ |
| UDCA | 6 | 790.16 ± 129.85$$ | 6.83 ± 0.75$$ |

Note:
N, sham-operation group; M, model group; HQT, astragalus soup group; A + B, A + B combination group; A, A alone group; B, B alone group; and UDCA, UDCA group.
*P < 0.05,
**P < 0.01 (vs N);
P < 0.05,
P < 0.01 (vs M);
$P < 0.05,
$$P < 0.01 (vs A + B).

TABLE 4

The changes of serum liver function in rats of each group

| group | n | ALT(U/L) | AST(U/L) | Alb(g/L) | ALP(K/100 ml) | TBil (μmol/L) |
|---|---|---|---|---|---|---|
| N | 8 | 14.58 ± 2.15 | 25.19 ± 5.47 | 36.48 ± 1.23 | 27.41 ± 6.00 | 7.30 ± 1.79 |
| 28dM | 7 | 64.45 ± 12.89** | 123.65 ± 15.72** | 22.51 ± 2.13** | 82.04 ± 8.90** | 74.59 ± 3.59** |
| HQT | 8 | 60.89 ± 16.03$ | 118.28 ± 20.64 | 27.68 ± 6.14# | 72.55 ± 5.74# | 60.44 ± 6.85## |
| A + B | 9 | 32.60 ± 10.34## | 105.92 ± 13.00# | 26.85 ± 3.67# | 71.65 ± 5.60# | 59.42 ± 10.14## |
| A | 8 | 42.82 ± 8.64$ | 116.43 ± 7.99# | 26.58 ± 4.09 | 71.94 ± 12.71# | 61.82 ± 7.89## |
| B | 6 | 26.66 ± 7.89## | 93.67 ± 14.46## | 25.07 ± 5.18 | 77.22 ± 4.05 | 67.35 ± 7.39$ |
| UDCA | 6 | 28.79 ± 8.61## | 102.80 ± 26.01# | 24.20 ± 3.64 | 79.01 ± 5.80 | 67.60 ± 9.62$ |

Note:
N, sham-operation group; M, model group; HQT, *astragalus* soup group; A + B, A + B combination group; A, A alone group; B, B alone group; and UDCA, UDCA group.
*P < 0.05,
**P < 0.01 (vs N);
P < 0.05,
P < 0.01 (vs M);
$P < 0.05,
$$P < 0.01 (vs A + B).

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of treating chronic liver disease in a subject, comprising administrating orally a therapeutically effective amount of a drug composition consisting of an Astragalus Astragaloside and a Glycyrrhiza acid to the subject.

2. The method, as recited in claim 1, wherein the Astragalus Astragalosides and the Glycyrrhiza Acid have a weight ratio of 3~6:1.

3. The method, as recited in claim 2, wherein the drug composition is prepared into clinical preparation which comprises tablets, granules, capsules or other oral solid preparation forms.

4. A method of treating liver fibrosis in a subject, comprising: administrating orally a therapeutically effective amount of a drug composition consisting of an Astragalus Astragaloside and a Glycyrrhiza acid to the subject.

5. The method, as recited in claim 4, wherein the Astragalus Astragalosides and the Glycyrrhiza Acid have a weight ratio of 3~6:1.

6. The method, as recited in claim 5, wherein the drug composition is prepared into clinical preparation which comprises tablets, granules, capsules or other oral solid preparation forms.

7. A method of treating liver cirrhosis in a subject, comprising: administrating orally a therapeutically effective amount of a drug composition consisting of an Astragalus Astragaloside and a Glycyrrhiza acid to the subject.

8. The method, as recited in claim 7, wherein the Astragalus Astragalosides and the Glycyrrhiza Acid have a weight ratio of 3~6:1.

9. The method, as recited in claim 8, wherein the drug composition is prepared into clinical preparation comprising tablets, granules, capsules or other oral solid preparation forms.

* * * * *